(12) United States Patent
Spector et al.

(10) Patent No.: US 11,771,447 B2
(45) Date of Patent: Oct. 3, 2023

(54) METHOD OF TREATMENT WITH LOW ENERGY EXTRACORPOREAL SHOCKWAVES

(71) Applicants: Avner Spector, Savyon (IL); Tamar Shultz More, Jerusalem (IL)

(72) Inventors: Avner Spector, Savyon (IL); Tamar Shultz More, Jerusalem (IL)

( * ) Notice: Subject to any disclaimer, the term of this patent is extended or adjusted under 35 U.S.C. 154(b) by 156 days.

(21) Appl. No.: 17/127,952

(22) Filed: Dec. 18, 2020

(65) Prior Publication Data
US 2021/0153885 A1 May 27, 2021

Related U.S. Application Data

(63) Continuation of application No. 14/938,494, filed on Nov. 11, 2015, now abandoned, which is a continuation-in-part of application No. 13/359,538, filed on Jan. 27, 2012, now abandoned.

(51) Int. Cl.
*A61B 17/22* (2006.01)
*A61H 23/00* (2006.01)

(52) U.S. Cl.
CPC ..... *A61B 17/22004* (2013.01); *A61H 23/008* (2013.01)

(58) Field of Classification Search
CPC .. A61B 17/22004; A61H 23/00; A61H 23/02; A61H 23/008; A61H 23/0245
See application file for complete search history.

(56) References Cited

U.S. PATENT DOCUMENTS

| | | | | |
|---|---|---|---|---|
| 6,390,995 | B1 * | 5/2002 | Ogden | A61B 17/2256 601/2 |
| 7,507,213 | B2 * | 3/2009 | Schultheiss | A61H 23/008 601/4 |
| 7,985,189 | B1 * | 7/2011 | Ogden | A61H 23/008 601/2 |
| 2006/0100550 | A1 * | 5/2006 | Schultheiss | A61B 17/22004 601/2 |
| 2006/0100552 | A1 * | 5/2006 | Schultheiss | A61H 23/008 601/2 |
| 2006/0246044 | A1 * | 11/2006 | Lutz | A61P 9/00 601/1 |
| 2007/0142753 | A1 * | 6/2007 | Warlick | A61N 7/00 601/2 |

FOREIGN PATENT DOCUMENTS

WO WO-2006034306 A2 * 3/2006 ....... A61B 17/22004

OTHER PUBLICATIONS

Kang, "Impaired Angiogenesis in the Remanant Kidney Model: II. Vascular Endothelial Growth Factor Administration Reduces Renal Fibrosis and Stabilizes Renal Function", pp. 1448-1457 of Journal of the American Society of Nephrology, 2001.*

* cited by examiner

Primary Examiner — Tu A Vo
(74) Attorney, Agent, or Firm — Shalom Wertsberger; Saltamar Innovations

(57) ABSTRACT

A method of treatment of the human or animal body with noninvasive low energy extracorporeal shockwaves and in particular, to such a method that is utilized for controlling a cascade of biomolecular activity involving a plurality of biomolecular factors, provided to improve function of the treatment portion of the human or animal body.

7 Claims, 9 Drawing Sheets
(3 of 9 Drawing Sheet(s) Filed in Color)

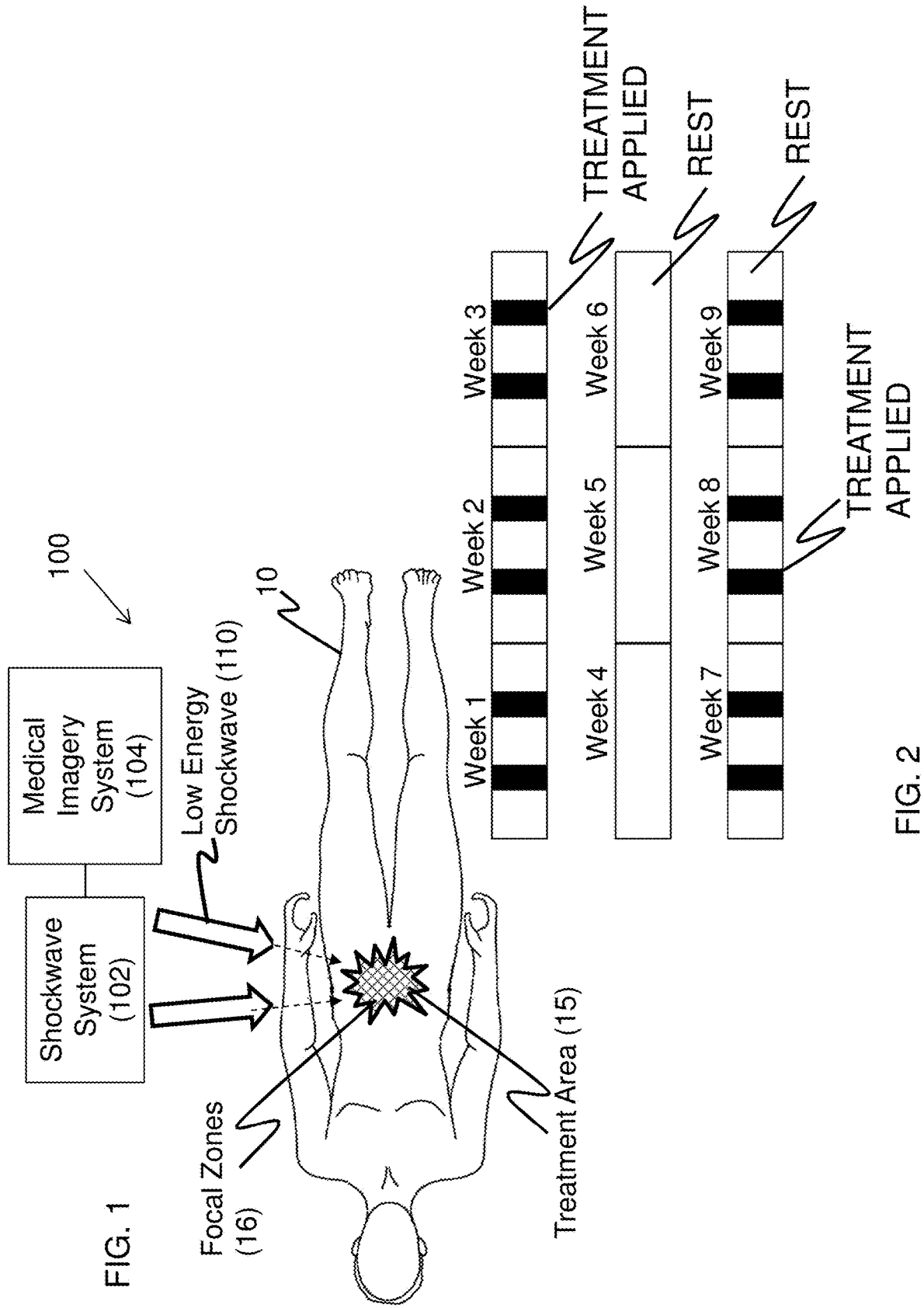

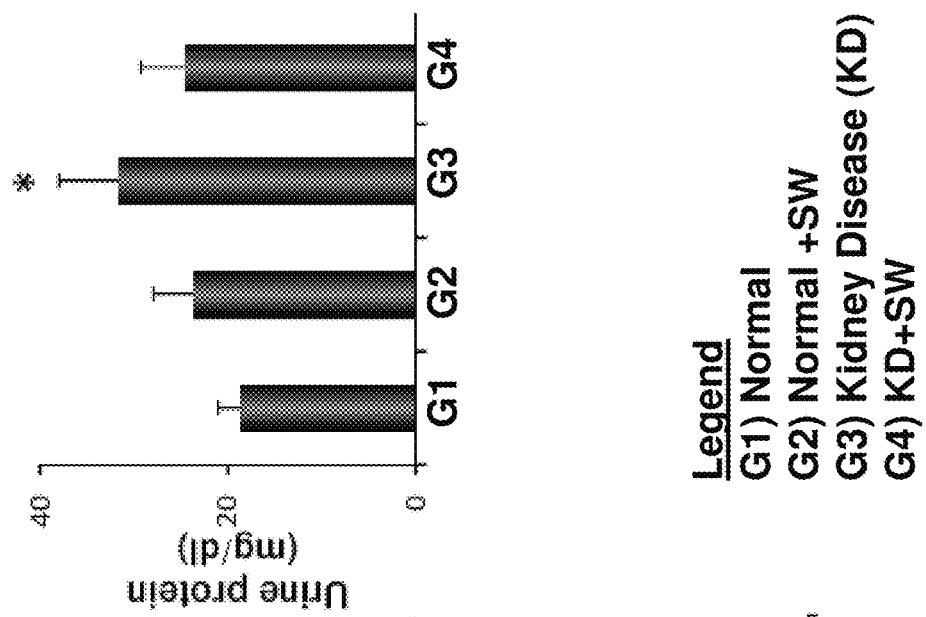
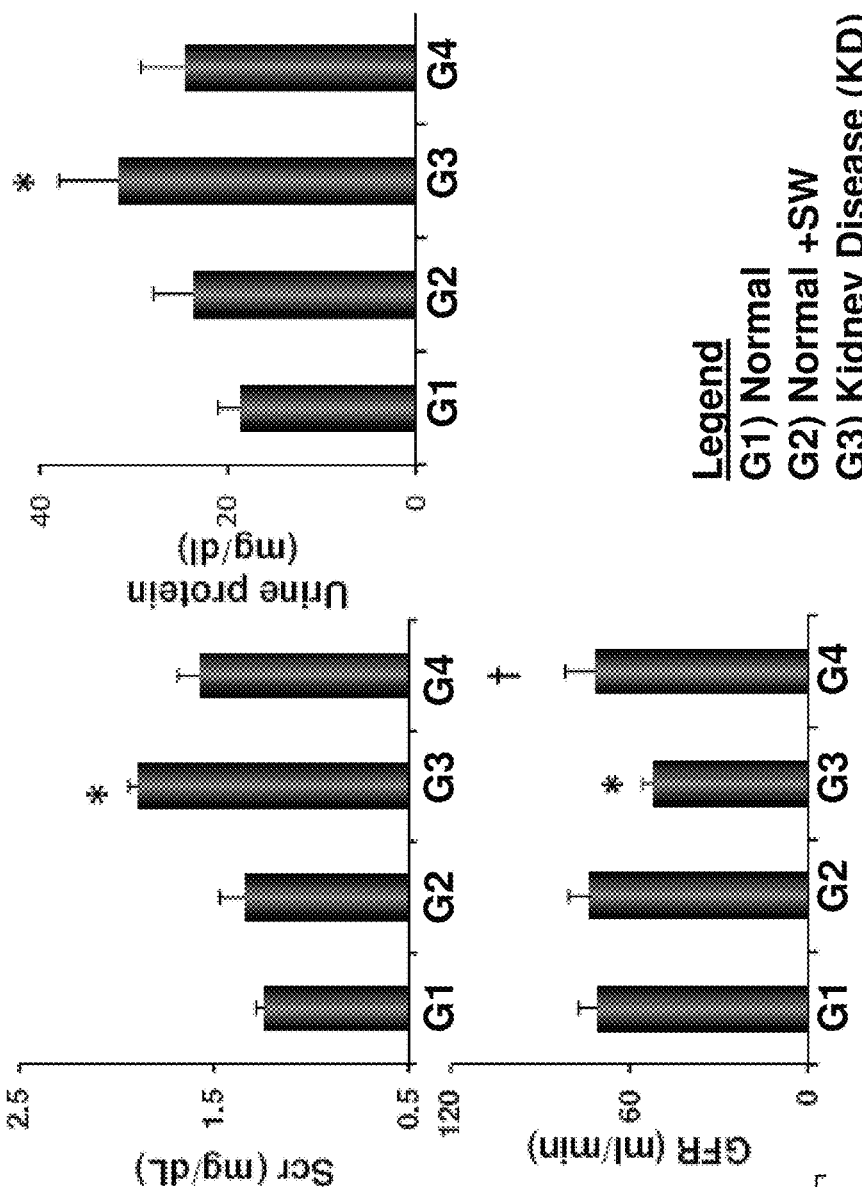
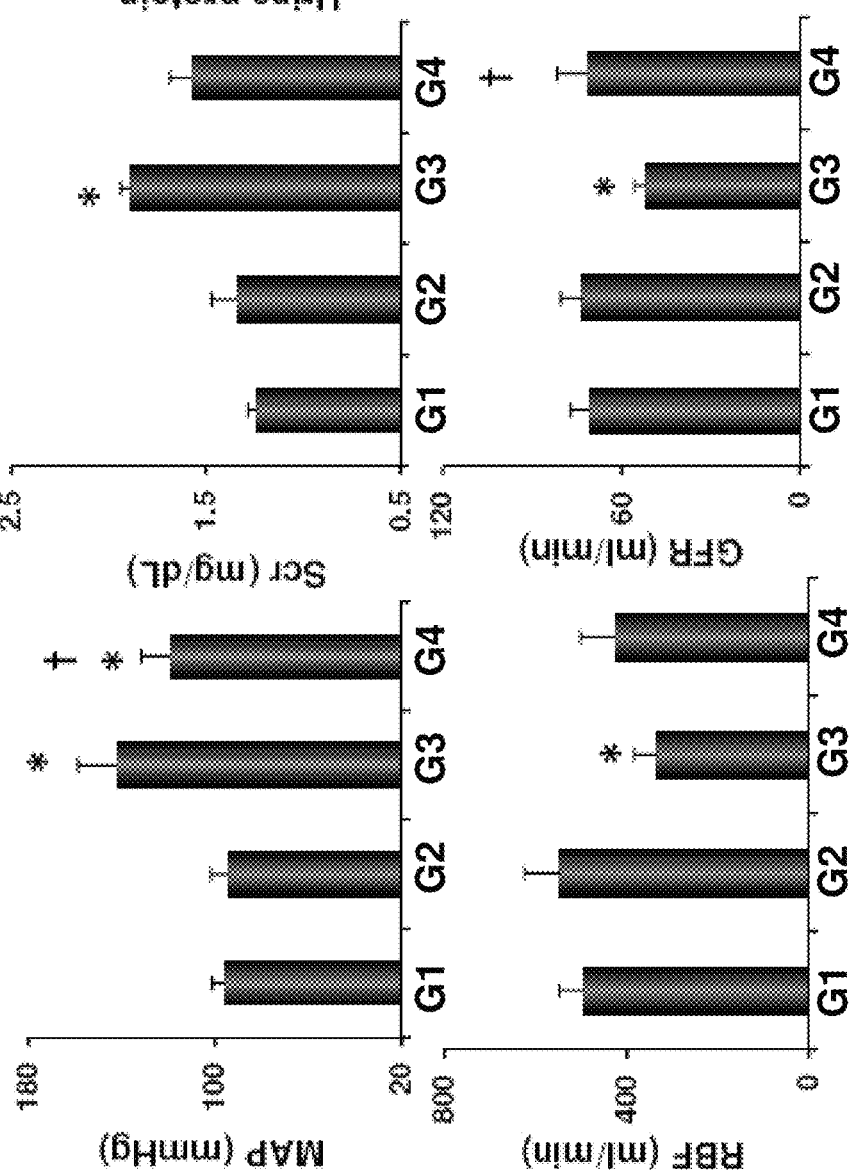

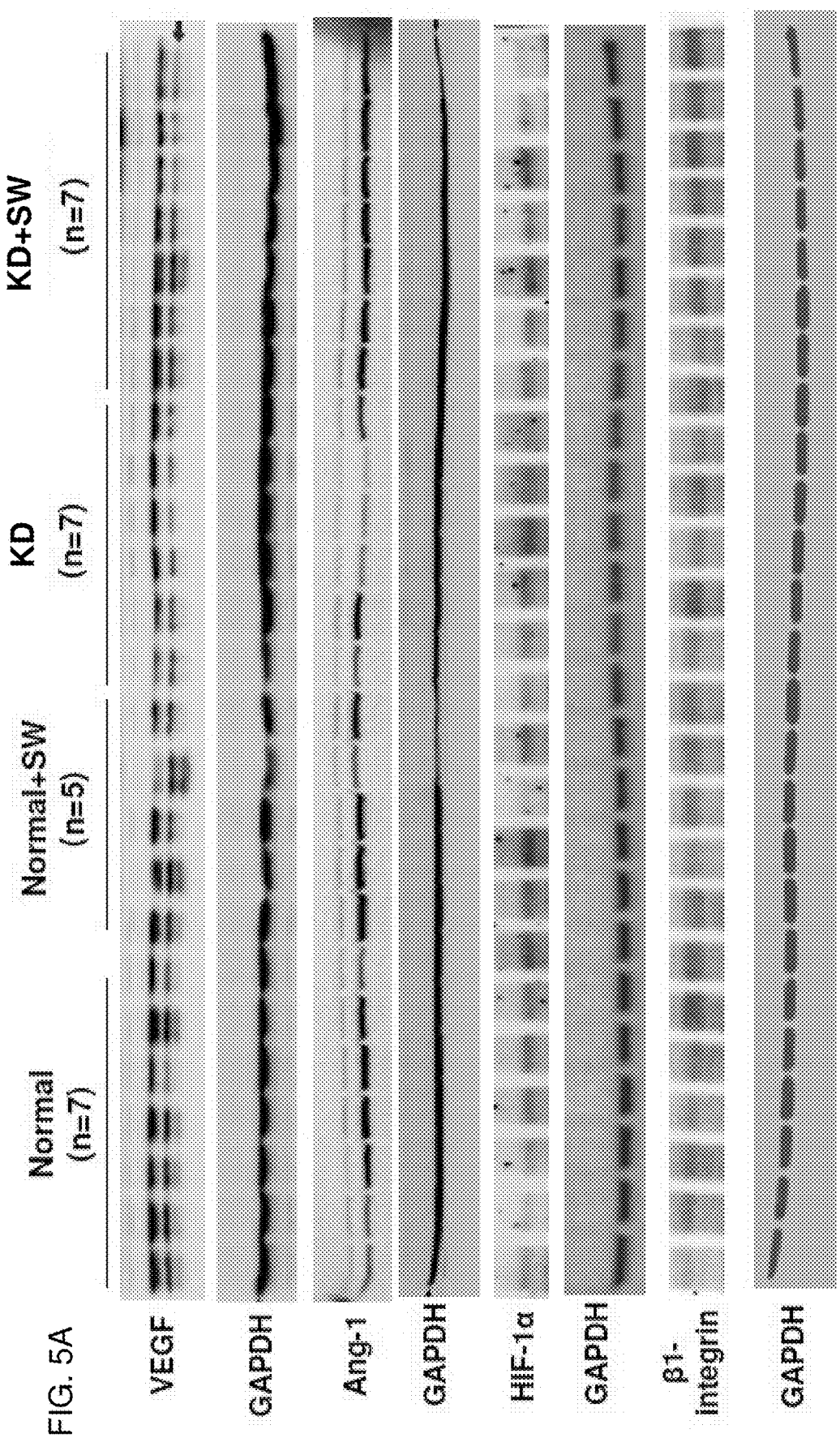

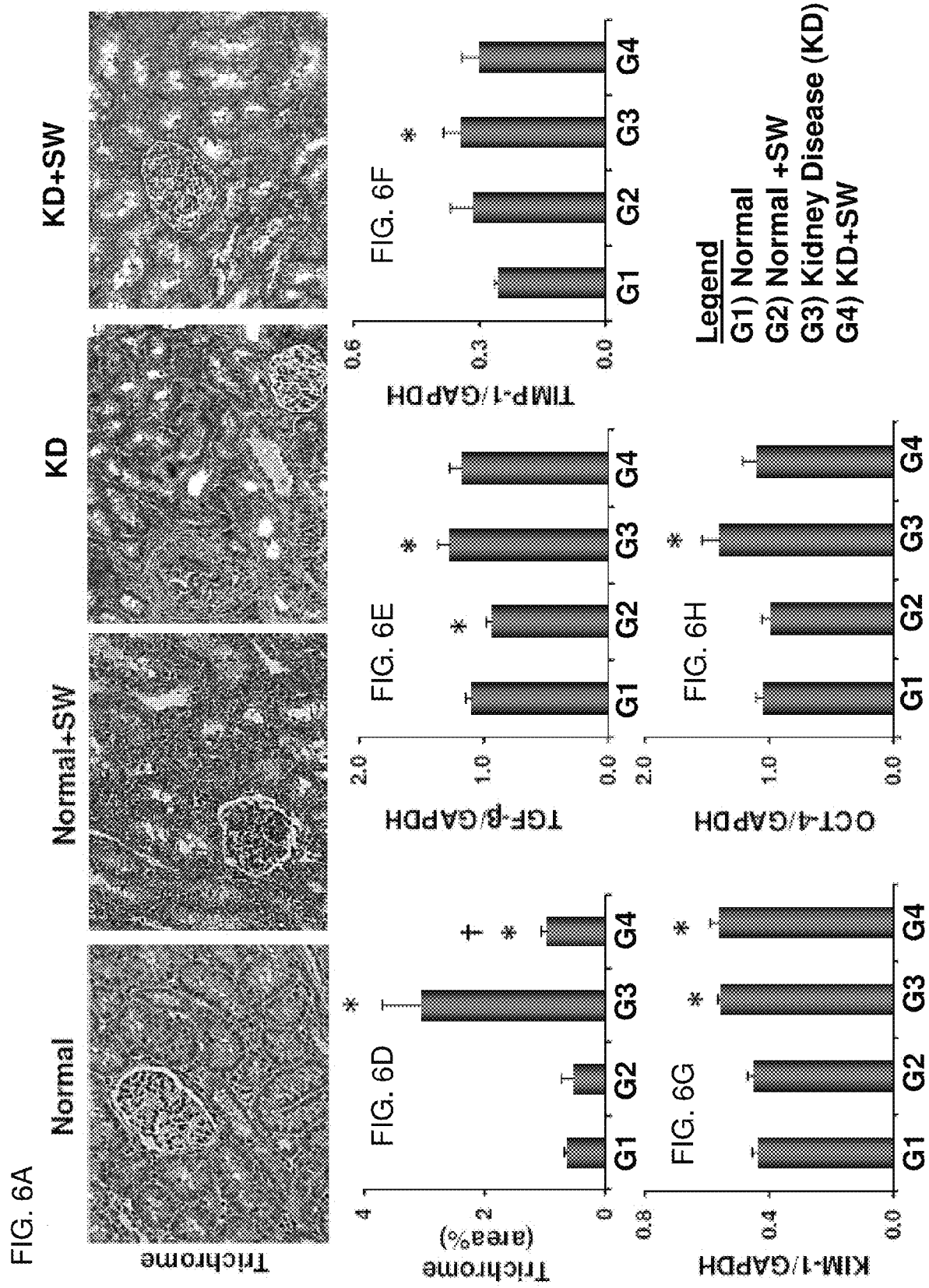

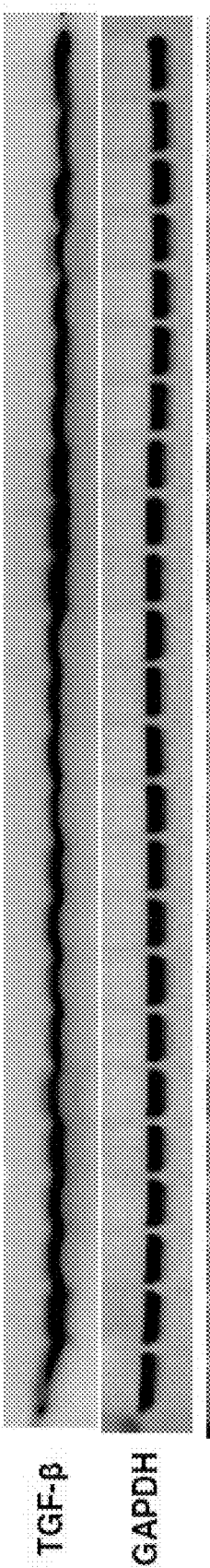
FIG. 6B
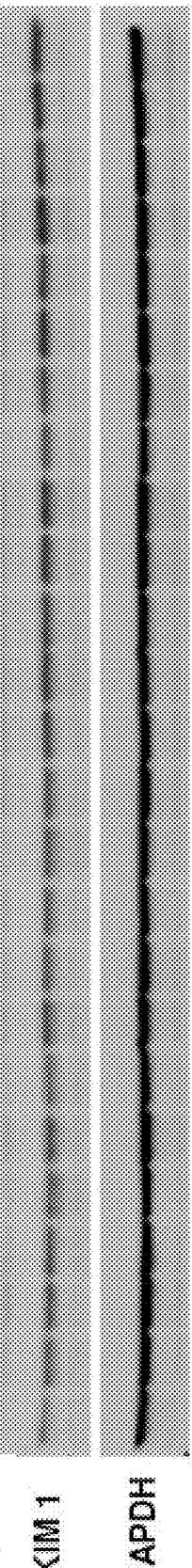
FIG. 6C
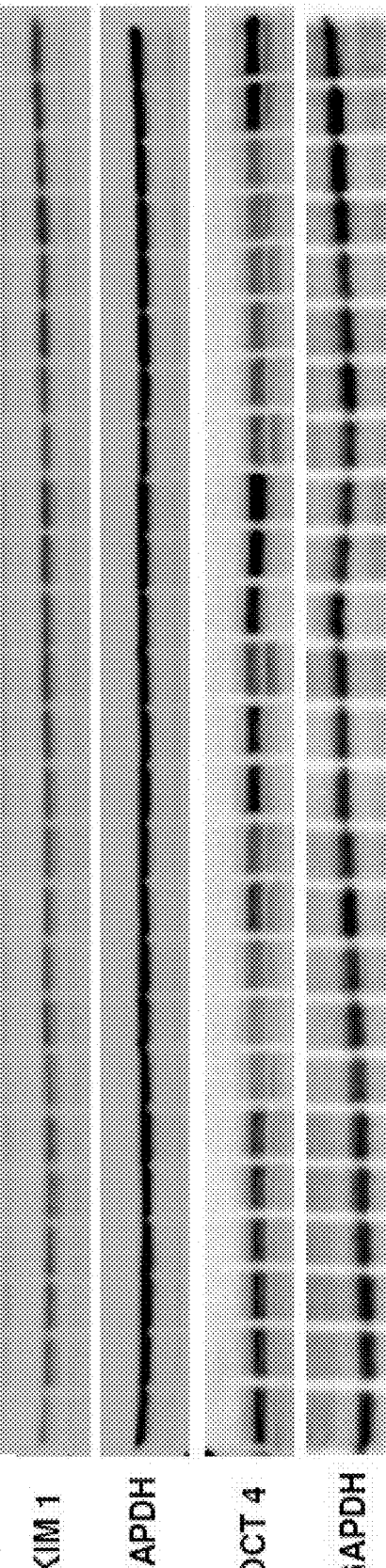

METHOD OF TREATMENT WITH LOW ENERGY EXTRACORPOREAL SHOCKWAVES

CROSS REFERENCE TO RELATED APPLICATION

This application is a Continuation of U.S. patent application Ser. No. 14/938,494, filed Nov. 11, 2015, which is in turn a Continuation In Part of U.S. patent application Ser. No. 13/359,538, filed Jan. 27, 2012, entitled "Method For Improving Kidney Function With Extracorporeal Shockwaves," the disclosure of both applications is incorporated herein by reference in their entirety.

FIELD OF THE INVENTION

The present invention relates to a method of treatment of the human or animal body with noninvasive low energy extracorporeal shockwaves and in particular, to such a method that is utilized for controlling a cascade of biomolecular activity involving a plurality of biomolecular factors.

BACKGROUND OF THE INVENTION

Extracorporeal shockwave therapy (herein referred to as 'ESWT') is non-surgical, non-invasive treatment of medical conditions using acoustic shockwaves. First use of shockwave therapy in the early 1980's was utilized to fragment kidney stones termed shockwave lithotripsy. Continued development of shockwave treatment showed the possibility of stimulating bone formation, angiogenesis, as well as other orthopedic indications. However, medical literature suggests that lithotripsy creates hypertension and some damage to the kidney including hematuria during the procedure.

A shockwave is a form of acoustic energy resulting from phenomena that create a sudden intense change in pressure for example an explosion or lightning. The intense changes in pressure produce strong waves of energy that can travel through any elastic medium such as air, water, human soft tissue, or certain solid substances such as bone.

Shockwaves are characterized by the delivery of a sequence of transient pressure disturbances characterized by an initial high peak pressure with a fast pressure rise followed by rapid wave propagation with diminishing amplitude over its lifecycle. Such that shockwaves characteristically have a quick lifecycle, starting with a big high amplitude pressure peak followed by a gradual diminishing pressure amplitude having amplitude of about 10-20% of the initial pressure peak. Shockwave are further characterized in that they do not produce heat within the tissue.

Shockwaves are therefore characteristically different from ultrasound in that the ultrasound waveform produces constant cyclic sinusoidal amplitude that produces heat at the tissue level. Conversely shockwaves do not have constant amplitude over time.

Acoustic shockwaves are primarily generated by three different methods, electrohydraulic (also referred to as spark gap), electromagnetic (also referred to as 'EMSE'), and piezoelectric. Each method needs an apparatus to focus the generated shockwave so as to provide a focal point and/or focal zone for the treatment area. In the focal zone shockwaves produce much higher pressure impulses as compared with the zones outside of the focal zone.

Mechanical means for focusing each of these methods is generally realized with an appropriate arrangement of surfaces reflecting the wave toward the desired focal point and/or an appropriate arrangement of the generating devices.

Spark gap systems incorporate an electrode (spark plug), to initiate a shockwave, and ellipsoid to focus the shockwave. EMSE systems utilize an electromagnetic coil and an opposing metal membrane. Piezoelectric systems form acoustical waves by mounting piezoelectric crystals to a spherical surface to provide focus. Of the three systems, the spark gap system is generally preferred in the art for generating therapeutic shockwaves ESWT as it introduces more of the generated shockwave energy to the treatment target site.

In spark gap systems, high energy shockwaves are generated when electricity is applied to an electrode positioned in an ellipsoid immersed in treated water. When the electrical charge is fired, a small amount of water is vaporized at the tip of the electrode and a shockwave is produced. The shockwave ricochets from the side of an ellipsoid and converges at a focal point, which may then be transferred to the area to be treated.

In electromagnetic systems an electrical impulse is circulated in a coil. The coil produces an electromagnetic field that expels a metallic membrane to produce the mechanical impulse.

In piezoelectric systems ceramic material with piezoelectric characteristics is subjected to an electrical impulse. The electric impulse modifies the dimension of the ceramic material to generate the desired mechanical impulse. A focal point is attained by covering a concave spherical surface with piezoelectric ceramics converging at the center of the sphere.

The method of focusing the generated shockwave has been greatly described in the art for example in U.S. Pat. Nos. 5,174,280 and 5,058,569, 5,033,456, EP1591070 all of which are incorporated herein by reference as if fully set forth.

Traditionally shockwaves have been used in medicine as a noninvasive means for treating a variety of anomalies such as kidney stones (lithotripsy), fragmentation of calcification, chronic orthopedic inflammation healing, bone healing (osteogenesis), wound healing, revascularization, angiogenesis are well known and described in medical literature.

U.S. Pat. No. 7,507,213 to Schultheiss, et al. discusses invasive stimulation of kidney by surgically exposing the organ for example heart or kidney prior to applying shockwave therapy.

US Patent Publication No. 2011/0257523 to Hastings et al. discusses a method utilizing high intensity focused ultrasound (HIFU) for ablating innervated tissue of the kidney, for denervating renal vasculature, including disruption and termination of renal sympathetic nerve activity, to improve cardiac and/or renal function particularly that associated with hypertension.

Traditional ESWT utilizes high energy shockwave, for example in the form of lithotripsy, to evoke high pressure shockwave with an energy density of about 0.6-1.1 $mJ/mm^2$. Application of low energy shockwave treatment (herein 'LESW') has been described by Krause U.S. Pat. No. 5,545,124 and Warlick in US Patent Publication No. 2007/0142753 for the treatment of pain and pancreatic tissue regeneration, respectively.

SUMMARY OF THE INVENTION

The present invention overcomes the deficiencies of the background by providing a method for treating a human or animal body with low energy extracorporeal shockwaves so as to control the cascade of biomolecular activity involving a plurality of biomolecular factors.

In embodiments of the present invention the low energy shockwave treatment is provided to at least a portion of a human or animal body over a treatment area in order to control the cascade of biomolecular activity in and around the treatment area so as to prevent the development of excess scar tissue and/or fibrosis in and around the treatment area. In particular the present invention provides a method for low energy shockwave treatment that is delivered to a treatment area exhibiting acute tissue trauma. Preferably such a method of treatment is provided for a precautionary and/or preventative treatment at an acute tissue trauma site that defines the treatment area so as to prevent development of fibrosis in and around the treatment area.

The application of low energy shockwave at an acute tissue trauma site, of a human or animal body, provides for triggering and controlling a cascade of molecular activity that is garnered to control Extra Cellular Matrix ('ECM') remodeling, in and around the treatment area. Preferably ECM remodeling is provided by the delivery of low energy shockwave at an acute tissue trauma site that in turn elicit a cascade of bio-molecular activity that controls the expression of at least one or more of: biomolecular factors, growth factors, ECM factors and/or ECM associated factors at the acute trauma site so as to allow for non-fibrotic tissue remodeling at the acute tissue trauma site.

In embodiments, the low energy shockwave treatment preferably provides for triggering a cascade of bio-molecular activity involving at least one growth factor and/or biomolecular factor selected from the group for example including but not limited to TGFβ; TIMP-1, FAK, SCF, HGF, FAK, or any combination thereof.

In embodiments, the treatment is preferably provided to downregulate TGFβ expression in and around the acute tissue trauma site so as to alleviate fibrotic tissue build up in and around the treated area and more preferably the acute tissue trauma site itself.

In embodiments, the treatment is preferably provided to downregulate TIMP-1 expression in and around the acute tissue trauma site so as to alleviate fibrotic tissue build up in and around the treated area and more preferably the acute tissue trauma site itself.

In embodiments, the treatment provides for delaying the cascade of biomolecular activity responsible for rendering fibrosis and/or fibrotic tissue build up in and around the treatment area and more preferably the acute tissue trauma site itself.

In embodiments, the treatment is preferably provided to downregulate TIMP-1 expression in and around the acute tissue trauma site.

In embodiments, the treatment protocol comprises an active treatment period where low energy shockwaves are delivered to the treatment area. Optionally the active treatment period may be followed by a period of rest, where no low energy shockwaves are delivered to the treatment area.

Optionally, the active treatment period may comprise at least one and optionally up to three week period, wherein each active treatment week includes at least one and up to four active treatment sessions, where low energy shockwaves are administered to at least a portion a human or animal body over at least one treatment area and/or at least one or more treatment zones.

Optionally each active treatment period is followed by an equal period of rest.

Optionally an active treatment period comprises a three week period of bi-weekly treatments and an optional a rest period comprising a three week period that is devoid of low energy shockwave treatments.

Optionally a treatment protocol may comprise a 9 week period including two active treatment periods around a rest period, where the length of each period is three weeks and wherein each treatment period includes bi-weekly active treatment session.

The treatment area may be divided into a plurality of individual treatment zones and/focal zones. Optionally the treatment area may be divided into a plurality of smaller focal zones based on a number of parameters for example including but not limited to treatment applicator head, size of treatment area the like or any combination thereof.

In embodiments each active treatment session may include at least 100 and up to about 500 low energy shockwaves that are administered over a single treatment focal zone, for example having a diameter of about 2 mm and up to about 15 mm. Optionally each active treatment session includes up to about 5000 low energy shockwaves that are administered over a treatment area.

In embodiments, the low energy shockwave treatment session are provided either before, after and/or during an acute trauma event. Preferably low energy shockwave treatment is administered to the tissue treatment area experiencing acute tissue trauma in a timely fashion following a tissue trauma event. Preferably low energy shockwave treatment is provided relative to the timing and/or onset of the acute tissue trauma, and may be before, during or after the acute tissue trauma event. Optionally the low energy shockwave treatment is provided within a 48 hour window from the occurrence of the acute trauma event. Optionally the treatment is provided within a 24 hour window from the occurrence of the acute trauma event. Optionally treatment with low energy shockwaves may be provided up to one week prior to an expected and/or planned procedure that causes acute tissue trauma, for example invasive medical intervention such as surgery, prostatectomy, hysterectomy, or the like acute tissue trauma event.

Optionally an initial treatment includes up to four treatment sessions is provided at the time of acute tissue trauma. Optionally follow up treatments may be provided following the initial treatment provided at the time of the tissue trauma event. Optionally the treatment may be provided as a complimentary treatment to compliment ongoing treatments and/or to prevent progression of a disease and/or improve initial results.

For example, a treatment protocol of up to four sessions is provided immediately following an acute tissue trauma associated with a myocardial infarction, each session consisting of at least 100 and up to 5000 shockwaves.

For example, a treatment protocol of at least two sessions is provided immediately following an acute tissue trauma associated with prostatectomy, each session consisting of at least 100 and up to 5000 shockwaves.

For example, a treatment protocol of four sessions is provided immediately following an acute tissue trauma associated with the kidney for example acute kidney failure, each session consisting of at least 100 and up to 5000 shockwaves.

For example, a treatment session two to three sessions is provided immediately following an acute tissue trauma as a result of acute kidney injury, each session consisting of at least 100 and up to 5000 shockwaves.

Optionally, the treatment may be provided to a human or animal body at any site of acute tissue trauma.

Optionally, the treatment may be provided to a human or animal body at any site of acute trauma as a result of medical intervention or surgery.

Optionally, the treatment may be provided to a human or animal body relative to any form of traumatic and/or invasive act of medical intervention. The low energy shockwave treatment may be provided before, after and/or during a tissue trauma event and/or an invasive act of medical intervention. For example, treatment may be provided up to one week prior to and/or before and/or in advance of a planned invasive medical intervention. For example treatment may be provided immediately after and/or during an act of invasive medical intervention. For example, treatment may be provided after and/or during the recovery period following an act of invasive medical intervention.

Optionally, the low energy shockwave treatment may be provided to a human or animal body prior to, following, or in combination with any form of pharmacological therapy for example including but not limited to chemotherapy, biological therapy and/or stem cell therapy, the like or any combination thereof.

Optionally, the acute trauma and/or acute tissue trauma event and/or invasive medical intervention may for example include but is not limited to heart surgery, angioplasty, prostatectomy, hysterectomy, acute kidney failure, acute kidney injury (AKI), suturing, removal of tissue ("ectomy"), cancer treatment, transplant the like or any combination thereof.

In embodiments the treatment according to the present invention may be provided for alleviating fibrosis as part of treatment for a medical condition selected from the group consisting of erectile dysfunction (ED), Kidney Disease (KD), chronic kidney disease (CKD), psoriasis, cardiac fibrosis, heart condition, pericarditis, cardiomyopathy, surgical procedures, transplants or the like.

In embodiment the treatment according to the present invention may be provided for alleviating fibrosis as part of treatment and/or for maintaining function of any cell, tissue or organ of the human or animal anatomy, for example including but not limited to heart, lung, kidney, liver, gall bladder, pancreas, spleen, stomach, intestine, gastrointestinal tract, lymphatic system, skeletal muscles, smooth muscles, cardiovascular system, urinary bladder, skin, female reproductive system, uterus, ovaries, fallopian tubes, cervix, male reproductive system, penis, vas deferens, testicles, prostate, or any portion, cell, tissue or functional group of the human or animal anatomy.

Optionally treatment protocol parameters may for example include but is not limited to the number of treatments sessions, the duration of a treatment protocol, timing of active and/or inactive treatment sessions, frequency of session, any combination thereof or the like.

Optionally the number of active treatment sessions may be provided from about 1 session to about 18 sessions. Optionally 12 active treatments may be provided during the treatment protocol according to the present invention. Optionally the number of active treatment session may for example be 1, or 2, or 3, or 4 or 5 or 6, or 7 or 8 or 9 or 10 or 11, or 12 or 13 or 14 or 15 or 16 or 17 or 18 or 19 or 20 or so sessions.

Optionally the duration of the treatment protocol according to the present invention may be from about 1 day up to about 18 weeks or the equivalent of 1 day up to about 126 days.

Optionally treatment may be provided periodically, continuously, sequentially, intermittently, according to a schedule comprising consecutive treatment sessions and/or with at least one or more intersession recesses and/or rest periods. Optionally the length of the recesses and/or rest period may vary according to the required treatment protocol.

Optionally, shockwave parameters may for example include but are not limited to number of shockwaves, frequency of shockwaves and intensity of the shockwave, or the like.

Preferably an initial treatment including up to four treatment sessions is provided at the time of acute tissue trauma. Optionally follow up treatments may be provided following the initial treatment provided at the time of the tissue trauma event. Optionally the treatment may be provided as a complimentary treatment to compliment ongoing treatments and/or to prevent progression of a disease and/or improve initial results.

The shockwave intensity may be provided from about 0.02 mJ/mm$^2$ to about 0.2 mJ/mm$^2$. Optionally and preferably shockwave intensity may be provided from about 0.09 mJ/mm$^2$ to about 0.11 mJ/mm$^2$. Optionally and more preferably shockwave intensity may be provided at about 0.1 mJ/mm$^2$.

Optionally shockwave pressure utilized in embodiments of the present invention may for example be from about 30 atm to about 200 atm and/or from about 3 Mpa to about 20 Mpa.

Optionally shockwave frequency may be provided from about 60 shockwaves per minute to about 360 shockwaves per minute. Optionally and preferably a shockwave frequency may be provided from about 120 shockwaves per minute to about 240 shockwaves per minute. Optionally and most preferably a shockwave frequency may be provided at about 180 shockwaves per minute.

Optionally shockwave frequency may be provided from about 1 Hz to about 6 Hz. Optionally and preferably a shockwave frequency may be provided at about 2-4 Hz. Optionally and preferably a shockwave frequency may be provided at about 2 Hz.

Optionally the number of shockwaves per treatment session may be provided from about 100 shockwave up to about 5000 shockwaves. Optionally about 1800 shockwaves per session may be provided.

Embodiments of the present invention provide a treatment of the human or animal body with low energy shockwaves, that are provided to improve and/or increase blood flow within the renal and/or kidney structures.

Optionally the low energy shockwaves delivered to at least a portion of a human or animal body during a treatment session according to the present invention may be applied to at least one or more treatment zone. Optionally a treatment area along the human or animal body may be divided into a plurality of individual treatment zones. Optionally the number of treatment zones utilized may be determined according to the size of the treatment area. Optionally the number of treatment zones utilized may be determined according to at least one or more parameter associated with the shockwave generating device and may for example include but is not limited to the shockwave device treatment head and its effective treatment zone capabilities. For example a treatment area may be divided into a plurality of smaller treatment zones, from about 5 up to about 15 treatment zones.

Optionally the overall number of shockwaves delivered to a treatment area may be distributed about a plurality of treatment zones in any manner required for the treatment, for example including evenly distributing the number of shockwaves based on the number of zones, or by unevenly distributing the number of shockwaves per zones, or the distribution of shockwaves may be based on the underlying tissues within the individual treatment zones, the like or any combination thereof. For example, a plurality of zones from about 5 to about 15 zones may be treated with 100 shockwaves to about 500 shockwaves within a treatment session to provide for a treatment protocol including up to about 5000 shockwaves to at least a portion of a human or animal body.

Optionally the shockwave treatment according to the present invention may be applied to at least a portion of a human or animal body from at least one or more optional approaches for example including but not limited to prone, lateral, supine, or any combination thereof, providing for appropriate non-invasive access to the portion of the human or animal body that is to be treated with low energy shockwaves.

Optionally the treatment according to the present invention may be applied to a renal structure selected from the group consisting of nephron, glomerulus, Bowman's capsule, tubules, medulla, renal artery, renal vein, renal pelvis, papilla, adrenal glands, adrenal cortex, adrenal medulla, phrenic arteries, and adrenal vein, neural tissue directly or indirectly innervating the kidney and renal structures, kidney neural system including renal sympathetic and renal para-sympathetic nerves, renal sympathetic nerves that lie within and immediately adjacent to the wall of the renal arteries.

Optionally the treatment may be directed at the glomerulus.

Optionally the treatment may be directed or otherwise adapted for applying treatment to the renal artery.

Optionally the method according to an optional embodiment of the present invention provides for the treatment of any one or more selected from the group comprising: kidney disease (KD), renal dysfunction, chronic kidney disease (CKD) at any stage (1-4), Renal Insufficiency, proteinuria, diabetic nephropathy on glomerulus, vascular lesions, glomerulus calcification, tubulo-interstitial lesions, reduced blood flow in the interlobular renal arteries, renal artery stenosis any combination thereof.

Optionally the method may provide for the reduction of the blood pressure of the patient.

Optionally the method may provide for the reduction of intra-glomerular hypertension.

Optionally the method may be provided for maintaining kidney function and/or improving kidney function and/or reduce kidney degradation, any combination thereof or the like.

Optionally the method may be provided for treating kidney disease (KD) at any stage.

Optionally the method may be provided for treating chronic kidney disease (CKD) at any stage, and/or hypertension.

Optionally the method may be provided for improving conditions associated with the kidney, renal structures.

Optionally the method may be provided to affect neural function or neural activity associated with the kidney structures.

Optionally the effects of the applied low energy shockwave treatment are selected from the group consisting of: regenerating neural tissue, normalization of neural function, normalization of neural activity, modification of neural function, modification of neural activity, regulating neural activity, regulating neural function, inhibiting neural activity, inhibiting neural function, promoting neural activity, promoting neural function, any combination thereof.

Within the context of this application the terms aqueous solution, aqueous medium, or aqueous environment may be used interchangeably to refer to an enclosure, opening, lumen, or space that is placed in an aqueous solution or mixture for example including but not limited to water, medicated water, ionized water, oil, gel, treated water or the like solution or mixture in a liquid state.

Within the context of this application the term extracorporeal shockwave therapy ('ESWT') refers to shockwave therapy provided with all forms of shockwave generating device.

Within the context of this application the term low energy extracorporeal shockwave therapy ('LESW') or low energy shockwave therapy or low intensity shockwave therapy may interchangeably refer to shockwave therapy provided with all forms of shockwave generating device and providing an energy density of up to about 0.20 $mJ/mm^2$.

Within the context of this application the term molecular factor or biomolecular factor refer to any one or more factors and/or its conformation or subunit thereof, for example including but not limited to mRNA, protein, molecule, receptor, transcription factor, enzyme, inhibitor, promotor, activator, repressor, regulating factor, protein, hormone, growth factor, chemokine, cytokine, kinase, transmembrane protein, membrane protein, stem cell, progenitor cell, or the like.

Within the context of this application, unless indicated otherwise, the term "molecular factor" or "biomolecular factor" may refer to any one or more of the following factors known in art: Transforming Growth Factor beta ('TGF-β' or 'TGFbeta'); Tissue Inhibitor of MetalloProteinases (TIMP); TIMP metallopeptidase inhibitor 1 (TIMP-1); Focal Adhesion Kinase ('FAK'); Stem Cell Factor ('SCF'); Hepatocyte Growth Factor ('HGF'); Stromal Derived Cell Factor 1 ('STF-1'); Octamer-Binding Transcription Factor 4 (Oct-4); Kidney Injury Molecule-1 (KIM-1); Stromal Cell-Derived Factor 1 (SDF-1) also known as C-X-C motif chemokine 12 (CXCL12); Hypoxia Inducible Factor 1 ('HIF-1'); Norepinephrine (NE); Integrin; Beta 1 integrin; Monocyte Chemoattractant Protein-1 ('MCP-1'); mRNA of the cluster of differentiation 3 T-cell co-receptor ('CD3 mRNA'); Vascular Endothelial Growth Factor (VEGF); Fibroblast Growth Factors (FGF); Endothelial Nitric Oxide Synthase (eNOS); Angiopoietins (Ang); platelet-derived growth factor; angiogenin; angiotropin; hepatocyte growth factor; platelet endothelial cell adhesion molecule; angiostatin; endostatin; thrombospondin; Chemokine family of the form CXC ('CXC'); Nitric Oxide ('NO'); Nuclear Factor Kappa-light-chain-enhancer of activated B cells ('NFkapaB'); Tumor Necrosis Factor Alpha mRNA ('TNF-alpha mRNA'); pigment epithelium, endothelial progenitor cell or the like.

Within the context of this application the term treatment area refers to an area of at least a portion of the human or animal body that is being treated with low energy shockwaves. Optionally the treatment area may be of any size, shape, volume. Such a treatment area may be divided into a number of smaller treatment zones that herein may be interchangeably referred to as sub-treatment zones, individual treatment zones and/or focal zones. A treatment zone and/or focal zone may be a portion of the human or animal body having a diameter of about 2 mm up and up to about 15 mm. A treatment area within the context of this application may receive up to about 5000 low energy shockwaves during a treatment session, while an individual treatment zone and/or focal zone may receive up to about 500 low energy shockwaves, during a treatment session.

Within the context of this application the term acute tissue trauma and/or acute tissue trauma event that occurs as a results of traumatic event may refer to any event affecting tissue causing acute tissue trauma. Such an acute tissue trauma event may for example include but is not limited to: medical intervention, blunt force trauma, lesion, invasive medical intervention, surgery, suture, myocardial infarction, acute kidney injury, hysterectomy, prostatectomy, biopsy, mastectomy, cancer treatment, chemotherapy, biological therapy, cell therapy, stem cell therapy, any combination thereof or the like.

Within the context of this application the term shockwave treatment device refers to a device comprising a controller and/or computer and a shockwave treatment applicator as is known in the art. For example, a shockwave treatment device comprises controller and/or computer that controls the shockwave treatment produced by the shockwave treatment applicator and/or treatment head.

Within the context of this application shockwave properties and/or parameters may be interchangeably represented in different units of measure as is accepted in the art to refer to the same and/or equivalent units of measure. For example shockwave pressure may be interchangeably provided in units of atmospheres ('atm') or Pascals ('pa') or mega Pascals (Mpa). Shockwave frequency may be provided in relative of absolute units, for example including but not limited to hertz ('Hz') and/or shockwaves per unit time, shockwave per minute, or the like.

Within the context of this application the term renal and/or kidney structures refers to any of the following structures nephron, glomerulus, Bowman's capsule, tubules, medulla, renal artery, renal vein, renal pelvis, papilla, adrenal glands, adrenal cortex, adrenal medulla, phrenic arteries, and adrenal vein, neural tissue directly or indirectly innervating the kidney and renal structures, kidney neural system including renal sympathetic and renal para-sympathetic nerves, renal sympathetic nerves that lie within and immediately adjacent to the wall of the renal arteries.

Within the context of this application the term human or animal body refers to any one or portion of any part, cell, tissue, system or organ associated with the human or animal anatomy, for example including but not limited to heart, lung, kidney, liver, gall bladder, pancreas, spleen, stomach, intestine, gastrointestinal tract, lymphatic system, skeletal muscles, smooth muscles, cardiovascular system, urinary bladder, skin, female reproductive system, uterus, ovaries, fallopian tubes, cervix, male reproductive system, penis, vas deferens, testicles, prostate, or any portion, cell, tissue or functional group of the human or animal anatomy. The human or animal body or portion thereof refers to any part, cell, tissue, system, or organ having in-vivo origin, in-vitro origin, as a result of a transplant, the like or any combination thereof.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. The patent or application file contains at least one drawing executed in color. Copies of this patent or patent application publication with color drawing(s) will be provided by the Office upon request and payment of the necessary fee.

In the drawings:

FIG. 1 is a schematic illustrative diagram of a portion of the human anatomy receiving the anti-fibrosis low energy shockwave treatment according to optional embodiment of the present invention;

FIG. 2 is a schematic illustrative diagram of a Gantt chart of an optional treatment protocol according to optional embodiments the present invention; FIG. 4A to FIG. 6H show results of a study showing the effects of the low energy shockwave treatment according to optional embodiments of the present invention as applied to the kidney of a pig study group. FIG. 4A-C shows response to low energy shockwave treatment of the KD+SW. FIG. 4D-E show overall improvement in kidney function as the KD+SW treatment group.

FIG. 5A-F show results of a study showing the effects of the low energy shockwave treatment according to optional embodiments of the present invention as applied to the kidney of a pig study group. FIG. 5A-F shows change in the renal expression of different biomolecular factors in response to low energy shockwave treatment; FIG. 5A shows the overall expression of the biomarkers; FIG. 5B-F provides graphical depiction of the results shown in FIG. 5A;

FIG. 6A-H show results of a study showing the effects of the low energy shockwave treatment according to optional embodiments of the present invention as applied to the kidney of a pig study group. FIG. 6A shows trichrome staining images of the different test groups. FIG. 6B shows renal expression of TGFbeta and TIMP-1 in the different test groups. FIG. 6C shows renal expression of KIM-1 and OCT-4. FIG. FIG. 6G-H provide a graphical depiction of results shown in FIG. 6C. FIG. 6D providing a graphical depiction of image shown in FIG. 6A. FIG. 6E-F provide a graphical depiction of image shown in FIG. 6B. FIG. 6G-H provide a graphical depiction of image shown in FIG. 6C.

DESCRIPTION OF THE PREFERRED EMBODIMENTS

Figure 3:
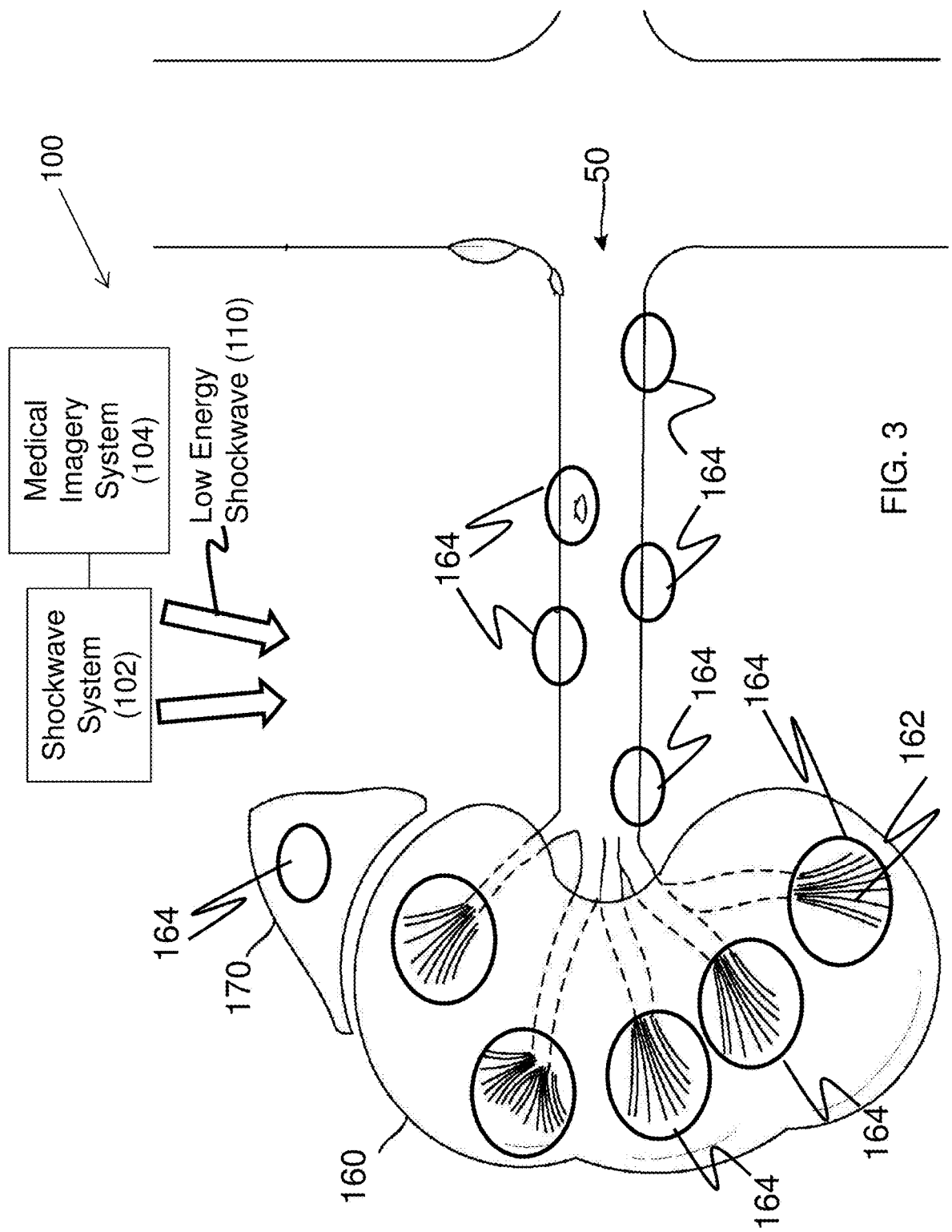
FIG. 3 is a schematic illustrative diagram of the kidney showing the kidney structures including the adrenal gland; and optional treatment zones involving the kidney.

The principles and operation of the present invention may be better understood with reference to the drawings and the accompanying description.

FIG. 1 provides an illustrative schematic diagram of the method according to embodiments of the present invention wherein a human or animal body 10 is treated with a shockwave treatment system 100 for providing low energy shockwave treatment to a treatment area and/or region 15 of the human or animal body 10.

In embodiments, the low energy shockwave treatment may be utilized to treat treatment area 15 that has undergone acute tissue trauma and/or is showing signs of fibrosis, while the treatment is provided so as to prevent the development of fibrosis in and around the treatment area 15 and/or to alleviate and reduce the level of fibrotic tissue build up in and around treatment area 15.

Optionally the method of the present invention further provides for improving blood flow in and around treatment area 15.

The method according to embodiments of the present invention includes the delivery of focused low energy shockwaves 110 produced with shockwave generating system 100 to the treatment area 15 so as to inhibit development of fibrosis in and around the treatment area 15.

The treatment area 15 may be found along any region along the anatomy of the human or animal body 10. The treatment wherein low energy shockwaves are applied may be provided from any approach for example including but not limited to prone, supine, lateral, the like or any combination thereof.

Optionally the applied treatment may be provided to alleviate progression of a fibrosis that has already developed.

Optionally the treatment may be provided to prevent and/or inhibit the development of fibrosis from developing in and around the treatment area 15 and in particular in an area of acute tissue trauma.

Optionally the treatment is provided with system 100 comprising a shockwave generating system and/or device 102 that may optionally be utilize under the guidance of a medical imagery system 104. Shockwave generating device 102 provides for generating low energy shockwaves 110 that are more preferably focused although they may optionally be non-focused, that are delivered with a treatment head and/or applicator known in the art (not shown). Medical imagery system and/or device 104 is optionally but preferably utilized to visually facilitate shockwave generating system 102 to generate shockwaves 110 to the appropriate treatment area 15 and/or focal zone 16 where treatment is to be applied. Medical imagery system 104 may be utilized to determine and define the location, size and shape of the treatment area 15 or focal zone 16.

Medical imagery system 104 may be provided in optional forms for example including but not limited to ultrasound, x-ray, computed tomography ('CT'), magnetic resonance ('MRI') or the like imaging technology and/or devices as is known and practiced in the art.

Shockwave generating system and/or device 102 may be provided in any form as is known in the art and may be provided in any form for example including but not limited to electrohydraulic (also referred to as spark gap), electromagnetic (also referred to as 'EMSE'), and piezoelectric, or the like shockwave generating technology and/or devices as is known in the art. Preferably device 102 utilizes a treatment applicator and/or treatment head (not shown) to deliver the generated shockwaves to the targeted treatment area 15, 16.

Shockwave generating system 102 is capable of producing low energy shockwaves 110 according to any shockwave parameters. Most preferably the shockwave parameters may for example include but are not limited to energy density (intensity), frequency, number of shockwaves, pressure, type of shockwave (focused or non-focused), the like or any combination thereof.

Optionally the low energy treatment is provided so as to treat and/or prevent fibrosis from developing over a treatment area 15. Most preferably the low energy shockwaves 110 to the treatment area 15 provide for treating fibrosis by enabling to control the biomolecular activity and/or signalizing pathway and/or cascade of biomolecular activity that is associated with fibrosis in and around the treatment area 15.

Optionally the low energy shockwave treatment provides for control of the biomolecular activity in and around treatment area 15, 16 and/or of the signaling pathway that involves and/or is associated with at least one or more of the bio-molecular factors selected from the group consisting of TGFbeta; TIMP-1, FAK, SCF, HGF, that are involved with fibrosis signaling pathway.

Most preferably the low energy shockwave treatment provides for control of the biomolecular activity of and/or signaling pathway associated with fibrosis that involves and/or is associated with at least one or more of the bio-molecular factors selected from the group consisting of TGFbeta; TIMP-1, FAK, SCF, HGF, that are involved with fibrosis signaling pathway.

Optionally, the cascade of bio-molecular activity is provided for reducing expression of TGFbeta. Optionally the reduction in TGFbeta expression is measurable from the onset of the treatment protocol. Optionally the expression of TGFbeta is gradually reduced over the course of the treatment.

Optionally control of the cascade of bio-molecular activity is provided for reducing expression of TIMP-1 at the onset of the treatment protocol.

Optionally control of the cascade of bio-molecular activity is provided for increasing expression of SCF through the treatment protocol.

Optionally control of the cascade of bio-molecular activity is provided for increasing expression of HGF through the course of the treatment protocol.

Optionally control of the cascade of bio-molecular activity is provided for modulating the expression and/or activation of FAK. Optionally control of the cascade of bio-molecular activity is provided for the activation of FAK. Optionally control of the cascade of bio-molecular activity is provided for controlling the activation of FAK as a function of the number of treatment sessions and/or number of shockwaves applied. Optionally control of the cascade of bio-molecular activity is provided for modulating the expression of FAK as a function of the number of treatment sessions and/or number of shockwaves applied. Optionally, FAK activation is provided and/or is measurable after the end of the treatment protocol is carried out. Optionally control of the cascade of bio-molecular activity is provided for controlling and/or modulating downstream activation of FAK as a function of the number of treatment sessions and/or number of shockwaves applied, wherein activation of FAK is realized and/or is measureable after a number of treatment sessions.

Optionally control of the cascade of bio-molecular activity is provided to cause increased expression of FAK.

Optionally control of the cascade of bio-molecular activity is provided to limit ECM expression in the treatment area 15.

Optionally control of the cascade of bio-molecular activity is provided to increase expression of ECM factors associated with collagen fibers.

Optionally control of the cascade of bio-molecular activity is provided to reduce ECM factors.

Optionally control of the cascade of bio-molecular activity is provided to reduce ECM factors and/or expression in the treatment area so as to allow for tissue remodeling in the treatment area.

Optionally control of the cascade of bio-molecular activity is provided to control and provide an overall reduction in ECM factors.

Optionally the cascade of molecular activity may further involve at least one or more of the following regulatory factors selected from the group consisting of: vascular endothelial growth factor (VEGF), fibroblast growth factors (FGF), angiopoietins (Ang), platelet-derived growth factor, angiogenin, angiotropin, hepatocyte growth factor, platelet endothelial cell adhesion molecule, angiostatin, endostatin, thrombospondin, CXC chemokines, Nitric oxide synthesis, NFkapaB activation, TNF-alpha mRNA expression, decreases the expression of MCP1, decrease expression of CD3 mRNA, and pigment epithelium.

The method according to the present invention provides for preventing the formation fibrosis in a human or animal body by applying low energy shockwaves treatment protocol over a treatment area 15 of the human or animal body with focused low energy shockwaves 110 having shockwave parameters including: an energy density from about 0.02 up to about 0.2 mJ/mm2, frequency of about 2 Hz.

Optionally the shockwave parameters utilized are energy density of about 0.09 to about 0.1 $mJ/mm^2$; at a frequency of about 2 Hz.

The treatment area 15 may be divided into a number of smaller treatment zones and/or sub-treatment zones 16, also referred to as focal zones. The number of sub-treatment zones may be based on the overall size of treatment area 15 for example including but not limited to the following parameters associated with size: diameter, volume, area, and/or shape, the like or any combination thereof. Optionally the diameter, size, area, volume and/or shape of each sub-treatment zone may determine the number of shockwaves applied to the treatment sub-zone.

The number of sub-treatment zones utilized may be based on technical specifications and/or parameters associated with the shockwave treatment device and in particular the treatment head and/or applicator. Optionally the number of treatment zones in a particular treatment area may be determined by the size of the treatment zone of the treatment head utilized for treatment.

FIG. 2 shows a schematic illustrating of a non-limiting treatment protocol according to the present invention where non-invasive low energy shockwave 110 treatment provided to inhibit fibrosis over a treatment area 15, or at least one or more focal zone 16. As shown, the treatment is provided over a span of 9 weeks and includes two active treatment periods between one period of rest, each period having a duration of three weeks, where each week includes two active treatment sessions of low energy shockwave treatment delivered to a treatment area 15. Optionally the treatments may include up to four active treatments per week.

The optional treatment protocol shown calls for two active treatment sessions per week during weeks 1, 2, 3, 7, 8, and 9, while no treatment is provided during weeks 4-6. Optionally the treatment protocol may comprise up to four active treatment session per week.

Optionally the treatment protocol may be personalized and/or configured by controlling the relative number of treatment periods and rest periods.

Optionally the treatment protocol may comprise a period of active treatment followed by a period of rest. Optionally the active treatment period is a three week period that includes bi-weekly treatments. Optionally each active treatment period is followed by an equal period of rest.

Optionally an active treatment period comprises a three week period of that includes up to four active treatment session where low energy shockwaves are delivered to a targeted treatment area 15 and/or treatment zone 16. Optionally a rest period comprises a three week period that is devoid of treatments.

Optionally the active treatment period may comprise at least one and up to three weeks, wherein each week includes at least one and up to four active treatment sessions, where low energy shockwaves are administered to a human or animal body 10 over a treatment area 15, 16.

Optionally the treatment protocol may be configured according to at least one or more parameters for example including but not limited to: length of active treatment period, number of active treatment sessions per week, length rest periods, frequency of rest period, number of shockwaves per treatment session, overall number of shockwaves delivered during active treatment period, the like or any combination thereof.

Optionally the treatment protocol may be configured according to the source of fibrosis, the stage of fibrosis when treatment is started, or the like factors associated with the fibrosis.

Optionally the number of active treatment sessions may be provided from about 1 session up to about 18 sessions. Optionally 12 active treatments may be provided during the treatment protocol according to the present invention. Optionally number of active treatment session may for example be 1, or 2, or 3, or 4 or 5 or 6, or 7 or 8 or 9 or 10 or 11, or 12 or 13 or 14 or 15 or 16 or 17 or 18 or 19 or 20 or so sessions.

Optionally the duration of the treatment protocol according to the present invention may be from about 1 day up to about 18 weeks or the equivalent of 1 day up to about 126 days.

Optionally treatment may be provided periodically, continuously, sequentially, intermittently, according to a schedule comprising consecutive sessions and/or with at least one or more intersession recesses and/or rest periods. Optionally the length of the recesses and/or rest periods may vary according to the required treatment protocol.

FIG. 3 provides an illustrative schematic diagram of the kidney and surrounding structures including kidney 160, adrenal gland 170, nephron and glomerulus 162, and renal artery 175. FIG. 3 further provides a schematic illustration of a plurality of optional focal zones and/or treatment zones 164 depicted about the kidney 100 and kidney structures associated with the kidney.

An optional embodiment of the present invention provides for applying non-destructive and non-invasive low energy shockwaves to such kidney structures and in particular to glomerulus 162, adrenal gland, 110 and renal artery 175, and the neural tissue associated with and/or innervating the kidney structures. Most preferably the low energy shockwave treatment improves overall kidney function.

Optionally the low energy shockwave treatment is provided to treat and/or maintain kidney function at its current level therein reducing kidney degradation due to chronic diseases such as hypertension, diabetes, and/or reduced kidney function.

Optionally the low energy shockwave treatment of the kidney according to the present invention further leads to an overall improvement in kidney function and/or conditions associated with the kidney and/or renal structures.

Optionally the low energy shockwave treatment according to the present invention may be provided to treat chronic kidney disease ('CKD') at any stage.

Optionally the low energy shockwave treatment according to the present invention may be provided to treat kidney disease ('KD') at any stage.

Optionally the low energy shockwave treatment according to the present invention may be provided to treat hypertension.

Optionally the low energy shockwave treatment according to the present invention may be provided to alleviate fibrosis in the kidney.

Most preferably the applied shockwaves are provided in a noninvasive, nondestructive manner, and do not cause tissue temperature elevation while utilizing low energy, low pressure amplitude, low energy shockwaves to bring about the treatment to the kidney structures.

Most preferably the low energy shockwave treatment according to the present invention is provided under the visual guidance of an imaging device or system 104 for example including but not limited to an ultrasound, CT, MRI or the like imaging technology and/or devices as is known and practiced in the art.

Most preferably imaging device and/or technology provides for aiding in defining the low energy shockwave treatment focal zone 16, 164 where treatment is to be applied for example including but not limited to the glomerulus 162, and/or adrenal gland 170, renal artery 175.

Optionally the shockwave treatment protocol may be focused on the glomerulus to bring about improved blood flow therethrough and associated kidney structures. Optionally the treatment according to the present invention may optionally further provide for removing glomerular calci.

Optionally the shockwave treatment protocol may be focused on the proximal tubules. Optionally the low energy shockwave treatment focused on the proximal tubules and/or glomerular podocytes provides for generating mechanical forces on the proximal tubules to elicit a cascade of biological activity leading to an angiogenic effects by upregulating FAK and VEGF, which in turn provides for improved blood flow.

Optionally the low energy shockwave treatment protocol according to the present invention may provide for the treatment of neural tissue and/or neural function of tissue associated with the kidney and kidney structures via optional pathways for example including but not limited to regenerating neural tissue and/or normalization of neural function and/or normalization of neural activity and/or modification of neural function and/or modification of neural activity and/or regulating neural activity and/or regulating neural functions and/or inhibiting neural activity and/or inhibiting neural function and/or promoting neural activity and/or promoting neural function, the like, or any combination thereof.

Optionally and preferably low energy shockwave treatment according to the present invention provides for a cascade of bio-molecular activity that brings about improved renal blood flow through the glomerulus and/or other renal structures and/or restored blood flow velocity in interlobular renal arteries.

Optionally a cascade of molecular activity that may for example, involve but is not limited to at least one or more of the following bio-molecular factors selected from the group: Transforming Growth Factor beta ('TGF-β' or 'TGF-beta'); Tissue Inhibitor of MetalloProteinases (TIMP); TIMP metallopeptidase inhibitor 1 (TIMP-1); Focal Adhesion Kinase ('FAK'); Stem Cell Factor ('SCF'); Hepatocyte Growth Factor ('HGF'); Stromal Derived Cell Factor 1 ('STF-1'); Octamer-Binding Transcription Factor 4 (Oct-4); Kidney Injury Molecule-1 (KIM-1); Stromal Cell-Derived Factor 1 (SDF-1) also known as C-X-C motif chemokine 12 (CXCL12); Hypoxia Inducible Factor 1 ('HIF-1'); Norepinephrine (NE); Integrin; Beta 1 integrin; Monocyte Chemoattractant Protein-1 ('MCP-1'); mRNA of the cluster of differentiation 3 T-cell co-receptor ('CD3 mRNA'); Vascular Endothelial Growth Factor (VEGF); Fibroblast Growth Factors (FGF); Endothelial Nitric Oxide Synthase (eNOS); Angiopoietins (Ang); platelet-derived growth factor; angiogenin; angiotropin; hepatocyte growth factor; platelet endothelial cell adhesion molecule; angiostatin; endostatin; thrombospondin; Chemokine family of the form CXC ('CXC'); Nitric Oxide ('NO'); Nuclear Factor Kappa-light-chain-enhancer of activated B cells ('NFkapaB'); Tumor Necrosis Factor Alpha mRNA ('TNF-alpha mRNA'); pigment epithelium, endothelial progenitor cell or the like Optionally the shockwave parameters utilized may be: a frequency of about 2 Hz and energy density from about 0.02 to about 0.2 mJ/mm2. Optionally the shockwave parameters utilized are energy density of about 0.09 to about 0.1 mJ/mm2; at a frequency of about 2 Hz.

Optionally each treatment session may comprise up to about 5000 shockwaves. Most preferably each treatment comprises about 2400 shockwave that are delivered to the kidney structure. Optionally the number of shockwaves per treatment session may be applied to at least one and more preferably a plurality of treatment zones 164 about the kidney structures. Optionally and more preferably a plurality of zones from about 5 up to about 15 zones may be treated during a treatment session. Optionally each zone may be treated with about 100 shockwaves to about 500 shockwaves, that may distributed amongst a plurality of zones from about 5 zones to about 15 zones forming the kidney structures.

Optionally the low energy shockwave treatment is provided for upregulating of canonical mechanotransducers selected from beta1-integrin and FAK.

Optionally the low energy shockwave treatment is focused on the proximal tubular cells of the treated kidney.

Optionally the low energy shockwave treatment further provides for activating VEGF to elicit angiogenesis in the treatment area.

Optionally the low energy shockwave treatment further provides for reducing mean arterial pressure (MAP).

Optionally the low energy shockwave treatment is utilized to normalize Plasma renin activity (PRA).

Optionally the low energy shockwave treatment is utilized to normalize levels of Norepinephrine Optionally the low energy shockwave treatment further provides for reducing serum creatinine and urinary protein excretion following treatment protocol.

Optionally the low energy shockwave treatment provides for improved renal blood flow (RBF) and GFR.

Optionally the low energy shockwave treatment provides for restoring microvasculature and improved renal oxygenation.

Optionally the low energy shockwave treatment provides for upregulating the expression of VEGF.

Optionally the low energy shockwave treatment provides for upregulating the expression of angiopoietin-1.

Optionally the low energy shockwave treatment provides for downregulate HIF-1 alpha.

Optionally the low energy shockwave treatment provides for restoring eNOS expression.

Optionally the low energy shockwave treatment provides for decreasing microvessel density in the kidney inner cortex and outer cortex.

Optionally the low energy shockwave treatment further provides for blunting renal oxygenation.

Optionally the low energy shockwave treatment provides the stimulation of mechanotransduction signaling pathways that provide for the upregulation of FAK and upregulation of beta1-integrin at different times, wherein beta1-integirn increases expression at the onset of the treatment protocol and wherein upregulation of FAK is provided at the end of the treatment protocol.

Optionally the low energy shockwave treatment is focused and targeted to the proximal tubules wherein the mechanical forces generated by the low energy shockwaves on the proximal tubules elicits a cascade of biological activity leading to an angiogenic effects by upregulating FAK and VEGF.

Optionally the low energy shockwave treatment provides for reduced renal fibrosis by down regulating the expression of at least one of TGFbeta or TIMP-1.

Optionally the low energy shockwave treatment provides for a reduction in OCT-4 activity.

Optionally the low energy shockwave treatment provides for controlling levels of SDF-1 beat level in the renal vein and inferior vena cava.

An optional embodiment of the present invention provides a method for treating a kidney exhibiting kidney disease, for example including but not limited to Atherosclerotic Renal Artery Stenosis (ARAS), in a human or animal body by applying low energy shockwaves treatment, the method comprising applying the low energy shockwave treatment having shockwave parameters including: an energy density from about 0.02 up to about 0.2 mJ/mm2, at a frequency of about 2 Hz; wherein the treatment delivers up to 5000 of the low energy shockwaves to trigger a cascade of bio-molecular activity improving the kidney disease.

Optionally the low energy shockwave treatment for treating kidney disease ARAS is provided for upregulating of canonical mechanotransducers selected from beta1-integrin and FAK.

Optionally the low energy shockwave treatment for treating kidney disease, for example including but not limited to ARAS, is focused on the proximal tubular cells of the treated kidney.

Optionally the low energy shockwave treatment for treating kidney disease, for example including but not limited to ARAS, further provides for activating VEGF to elicit angiogenesis in the treatment area.

Optionally the low energy shockwave treatment for treating kidney disease, for example including but not limited to ARAS, further provides for reducing mean arterial pressure (MAP).

Optionally the low energy shockwave treatment for treating kidney disease, for example including but not limited to ARAS, is utilized to normalize Plasma renin activity (PRA).

Optionally the low energy shockwave treatment for treating kidney disease, for example including but not limited to ARAS, is utilized to normalize levels of Norepinephrine Optionally the low energy shockwave treatment for treating kidney disease, for example including but not limited to ARAS, further provides for reducing serum creatinine and urinary protein excretion following treatment protocol.

Optionally the low energy shockwave treatment for treating kidney disease, for example including but not limited to ARAS, provides for improved renal blood flow (RBF) and GFR.

Optionally the low energy shockwave treatment for treating kidney disease, for example including but not limited to ARAS, provides for restoring microvasculature and improved renal oxygenation.

Optionally the low energy shockwave treatment for treating kidney disease, for example including but not limited to ARAS, provides for upregulating the expression of VEGF.

Optionally the low energy shockwave treatment for treating kidney disease, for example including but not limited to ARAS, provides for upregulating the expression of angiopoietin-1.

Optionally the low energy shockwave treatment for treating kidney disease, for example including but not limited to ARAS, provides for downregulate HIF-1 alpha.

Optionally the low energy shockwave treatment for treating kidney disease, for example including but not limited to ARAS, provides for restoring eNOS expression.

Optionally the low energy shockwave treatment for treating kidney disease, for example including but not limited to ARAS, provides for decreasing microvessel density in the kidney inner cortex and outer cortex.

Optionally the low energy shockwave treatment for treating kidney disease, for example including but not limited to ARAS, further provides for blunting renal oxygenation.

Optionally the low energy shockwave treatment for treating kidney disease, for example including but not limited to ARAS, provides the stimulation of mechanotransduction signaling pathways that provide for the upregulation of FAK and upregulation of beta1-integrin at different times, wherein beta1-integirn increases expression at the onset of the treatment protocol and wherein upregulation of FAK is provided at the end of the treatment protocol.

Optionally the low energy shockwave treatment for treating kidney disease, for example including but not limited to ARAS, is focused and targeted to the proximal tubules wherein the mechanical forces generated by the low energy shockwaves on the proximal tubules elicits a cascade of biological activity leading to an angiogenic effects by upregulating FAK and VEGF.

Optionally the low energy shockwave treatment for treating kidney disease, for example including but not limited to ARAS, provides for reduced renal fibrosis by down regulating the expression of at least one of TGFbeta or TIMP-1.

Optionally the low energy shockwave treatment for treating kidney disease, for example including but not limited to ARAS, provides for a reduction in OCT-4 activity.

Optionally the low energy shockwave treatment for treating kidney disease, for example including but not limited to ARAS, provides for controlling levels of SDF-1 beat level in the renal vein and inferior vena cava.

Example I—Fibrosis Prevention Due to Acute Tissue Trauma

The treatment protocol according to the present invention may be provided to prevent fibrosis from developing in an area of acute tissue trauma, for example as a result an invasive medical intervention procedure such as surgery, for example an prostatectomy.

Preferably immediately following the completion of the medical procedure the area undergoing the procedure is treated with at least 100 and up to about 2000 low energy shockwaves, and optionally up to about 5000 low energy shockwaves during an active treatment session. The low energy shockwave treatment is repeated for treatment course including at least 2 active treatment sessions following the procedure, preferably within three weeks and/or 21 days following the prostatectomy. Optionally and more preferably the active treatments continue thereafter with at least 6 (six) active treatment sessions during the rehabilitation period following the procedure and preferably performed over a span of at least 6 weeks.

Optionally the treatment may be preceded by a preventative and/or preparatory treatment with low energy shockwave treatment that may be provided up to about one week prior to the acute tissue trauma event. Optionally treatment with low energy shockwaves including at least 100 and up to about 2000 low energy shockwaves, and optionally up to about 5000 low energy shockwaves, that may be provided to a portion of the human or animal body that is expected to undergo a planned medical procedure that causes acute tissue trauma, for example invasive medical intervention such as surgery, prostatectomy, hysterectomy, or the like acute tissue trauma event.

Preferably, applying the treatment immediately at the end of the invasive treatment and/or tissue trauma event, and optionally providing treatment in advance of the tissue trauma event, allows for altering the cascade of bio-molecular activity, most preferably to downregulate the expression of at least TGFbeta and more preferably both TGFbeta and TIMP-1, immediately with the onset of treatment. Optionally immediate treatment following trauma further provides for preventing fibrosis by modulating expression of FAK relative to the onset of the traumatic event. Optionally modulating expression of FAK may for example include but is not limited to delaying the elevation of expression of FAK.

Example II—Fibrosis Alleviation Due to Existing Fibrosis

The treatment protocol according to the present invention may be provided to alleviate and/or slow down the advancement of fibrosis in biological tissue of the human or animal body. Preferably tissue exhibiting fibrosis and/or fibrotic tissue at various levels of fibrosis, may be treated with low energy shockwaves so as to alter the cascade of bio-molecular activity at the site of fibrosis so as to enhance ECM remodeling within the treatment area so as to alleviate fibrosis.

Optionally the treatment protocol comprises at least three weeks of treatment sessions where each week includes up to four active treatment session, so as to reduces expression of TGFbeta and TIMP-1, wherein each active treatment session includes the delivery of up to about 5000 low energy shockwaves, having an energy density profile from about 0.02 mJ/mm2 up to about 0.2 mJ/mm2 that are delivered at a frequency of about 2 Hz. Optionally the active treatment session may be followed by a rest period including no treatments. Optionally the rest period may have a length of at least one week and up to about three weeks.

Example III—Treatment of Kidney Disease (KD) with Low Enemy Shockwave Treatment

FIG. 4A to FIG. 6H show results of a study showing the effects of low energy shockwave treatment applied to the kidney of a pig suffering from Kidney Disease (KD). The results depicted herein shows how the treatment provides for controlling the cascade of biomolecular activity involving a plurality of biomolecular factors, by applying low energy shockwave treatment to the kidney, using the treatment and shockwave parameters as described above. The treatment effects are shown when comparing the following test groups: untreated Normal pigs ('Normal', 'G1'), Normal pigs treated with the low energy shockwave treatment ('Normal+SW', 'G2'), untreated pigs exhibiting Kidney Disease ('KD', 'G3') and pigs exhibiting Kidney Disease that were treated with the low energy shockwave treatment ('KD+SW', 'G4'). The treatment groups were treated with six low energy shockwave sessions over a three week period, where each week consisted of two active treatment sessions.

FIG. 4A-C shows response to low energy shockwave treatment of the KD+SW study group, in particular showing the treatment effects that lowered the mean arterial pressure (MAP) as shown FIG. 4A, lowered serum creatinine (SCR) as shown FIG. 4B, and lowered urine protein excretion levels as showing in FIG. 4C. All showing signs of overall improvement of general kidney function.

FIG. 4D-E similarly show overall improvement in kidney function as the KD+SW treatment group increased renal blood flow (RBF) as shown in FIG. 4D and glomerular filtration rate (GFR) in the KD+SW group as shown in FIG. 4E.

Figures 4F, 4G:
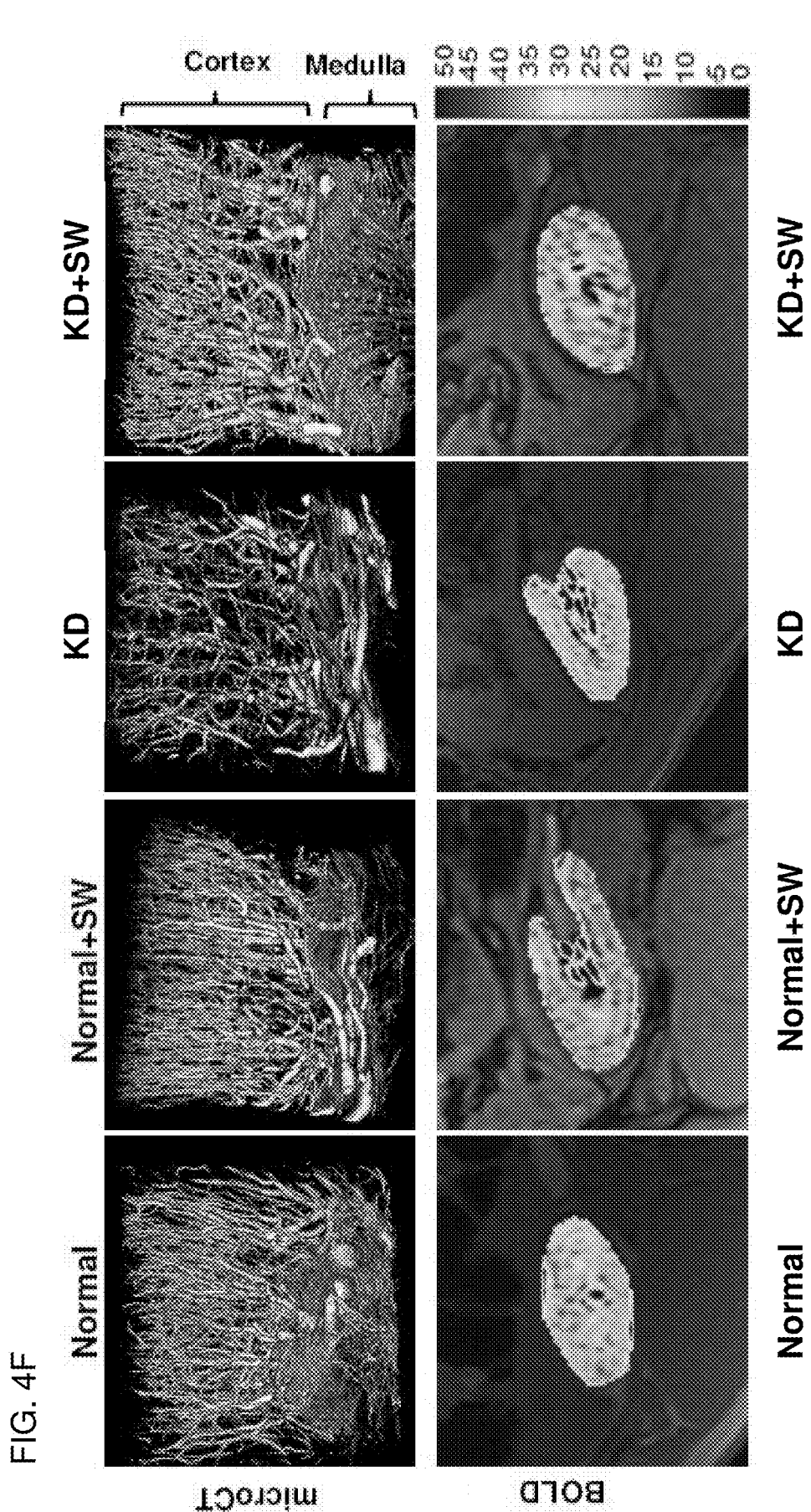
FIG. 4F shows micro-CT images of each of the test groups.
FIG. 4G shows MRI images of each of the test groups.

FIG. 4F shows micro-CT images of each of the test groups showing that the KD+SW treatment group exhibited statistically significant increase in the microvascular density.

FIG. 4G shows MRI images of each of the test groups shows blood oxygen dependent MRI imaging indicating that the KD+SW treatment group exhibited statistically significant increase in kidney oxygenation levels.

Figure 4I:
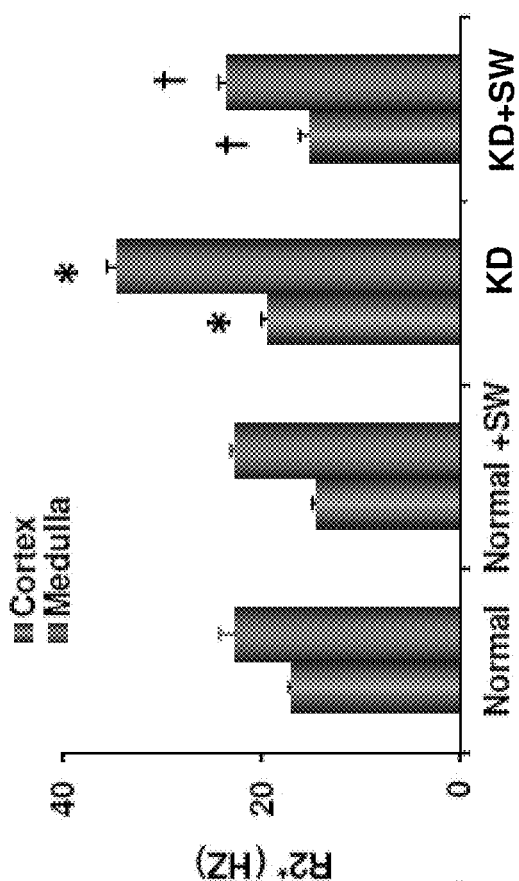
Figure 4H:
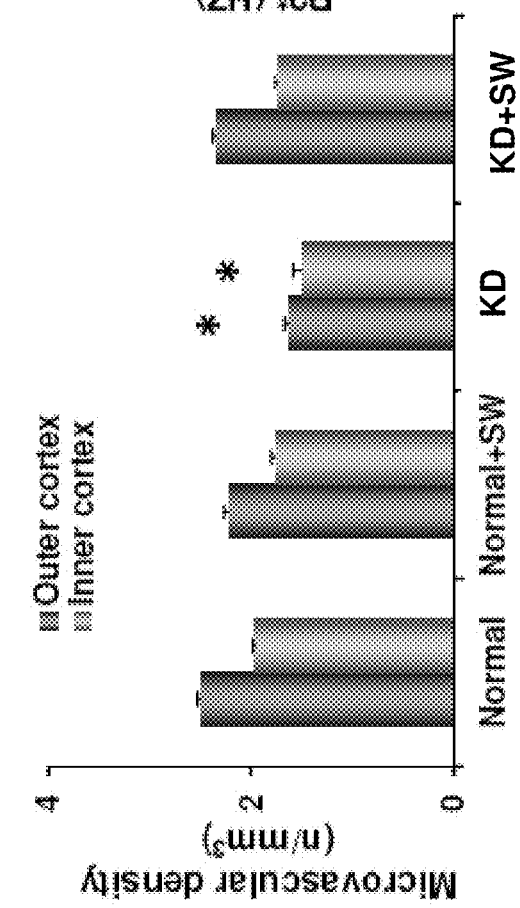
FIG. 4H provides a graphical depiction of the FIG. 4F showing change in the microvascular density in the different test groups.

FIG. 4H provides a graphical depiction of the change in the microvascular density in the different test groups, paralleling the images shown in FIG. 4F, where the microvascular density is seen between KD group and the KD+SW group, in different regions of the kidney.

FIG. 4I provides a graphical depiction of the change in the microvascular density in the different test groups, paralleling the images shown in FIG. 4F-G, where the microvascular density and increased kidney oxygenation as measured by hypoxia R2 as seen between KD group and the KD+SW group in different regions of the kidney.

Figures 5B, 5C, 5D, 5E, 5F:
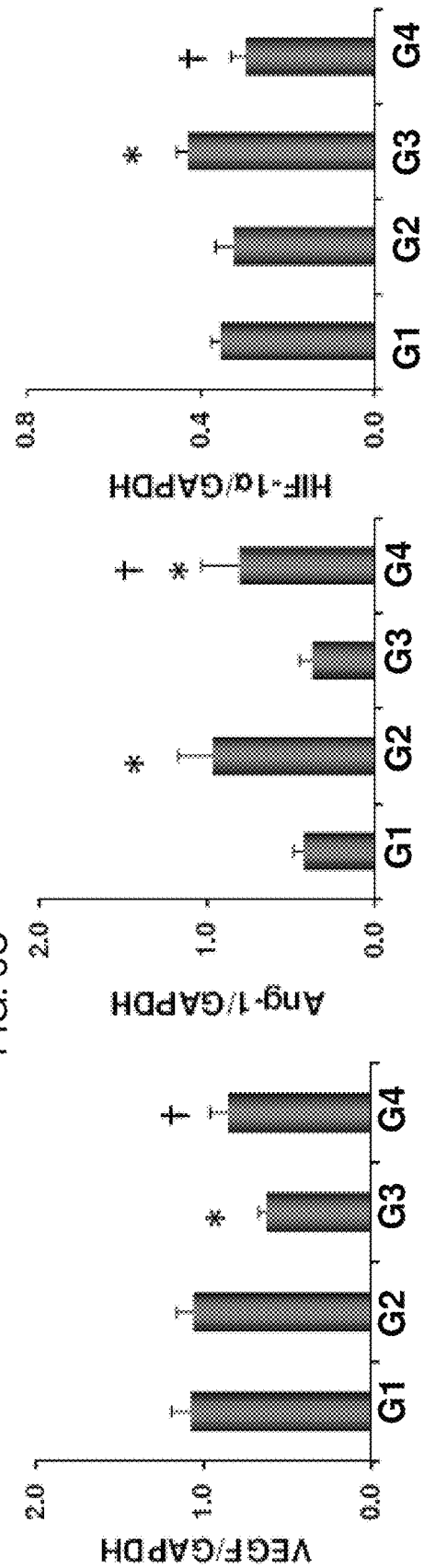

FIG. 5A-F shows change in the renal expression of different biomolecular factors in response to low energy shockwave treatment, in the different test groups. FIG. 5A shows the overall expression of VEGF, Ang-1, HIF-1 alpha, Beta1-integrin.

FIG. 5B-F provides graphical depiction of the results shown in FIG. 5A. Accordingly shockwave treatments was seen to restore and/or increase expression of VEGF as shown in FIG. 5B, increase levels of Ang-1 as shown in FIG. 5C, attenuated and/or diminished expression of HIF-1 alpha as shown in FIG. 5D, upregulated beta1-integrin as shown in FIG. 5E, and upregulated FAK as shown in FIG. 5F.

FIG. 6A shows trichrome staining images of the different test groups, where trichrome staining is indicative of fibrotic tissue. As seen in FIG. 6A there is a significant decrease in fibrotic tissue when comparing the KD group with the KD+SW groups. This is similarly seen in FIG. 6D providing a graphical depiction of the images, indicating that low energy shockwave treatment reduces and/or alleviates fibrosis and/or fibrotic tissue build up.

FIG. 6B shows renal expression of TGFbeta and TIMP-1 in the different test groups, that is also shown graphically in FIG. 6E showing TGFbeta, and FIG. 6F showing TIMP-1, the images showing decreased expression of both TGFbeta and TIMP-1 as a result of the low energy shockwave treatment.

FIG. 6C shows renal expression of KIM-1 and OCT-4 in the different test groups. FIG. 6G-H provide a graphical depiction of results shown in FIG. 6C, where FIG. 6G, shows expression of KIM-1 and FIG. 6H shows expression of OCT-4, both indicating a decrease in expression of both KIM-1 and OCT-4 as a result of the low energy shockwave treatment.

While the invention has been described with respect to a limited number of embodiment, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not described to limit the invention to the exact construction and operation shown and described and accordingly, all suitable modifications and equivalents may be resorted to, falling within the scope of the invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Citation or identification of any reference in this application shall not be construed as an admission that such reference is available as prior art to the invention.

Section headings are used herein to ease understanding of the specification and should not be construed as necessarily limiting.

What is claimed is:

1. A method for preventing an onset of formation of renal fibrosis in a human or animal body for individuals suffering from cancer and as part of a cancer treatment protocol, the method comprising applying a low energy shockwave treatment protocol over a treatment area of at least a kidney of the human or animal body prior to applying a cancer treatment protocol selected from chemotherapy, biological therapy, cell therapy, or stem cell therapy, and wherein said treatment area having or expected to have acute tissue trauma,
   a) the low energy shockwave treatment protocol having shockwave parameters including: an energy density from 0.02 and up to 0.2 milliJoules per millimeter squared (mJ/mm2), at a frequency of 2 Hertz (Hz);
   b) wherein the low energy shockwave treatment protocol applies a number of low energy shockwaves, wherein the number of applied shockwaves is up to 5000 shockwaves, over at least a portion of the treatment area, and wherein the low energy shockwaves are delivered to the treatment area triggering a cascade of bio-molecular activity involving at least one bio-molecular factor selected from the group consisting of: Transforming Growth Factor beta (TGFbeta); Tissue Inhibitor of MetalloProteinases inhibitor1 (TIMP-1), Focal Adhesion Kinase (FAK), Stem Cell Factor (SCF), Hepatocyte Growth Factor (HGF), the cascade of bio-molecular activity operative to prevent or alleviate fibrosis in and around the treatment area wherein at least one of TGFbeta or TIMP-1 is reduced in expression or wherein of at least one of SCF, HFG or FAK is increased in expression; and
   c) wherein said low energy shockwave treatment protocol is initiated within either a 48 hour window or at least one week prior to the cancer treatment protocol.

2. The method of claim 1 wherein said treatment area is divided into a plurality of small treatment zones, wherein each treatment zone is provided with at least 100 shockwaves and up to 500 shockwaves.

3. The method of claim 1 wherein said low energy shockwave treatment protocol is provided in three week treatment phases wherein each week includes up to four treatment sessions.

4. The method of claim 1 wherein said low energy shockwave treatment is provided over a span of up to 9 weeks.

5. The method of claim 4 wherein the low energy shockwave treatment protocol includes up to four active treatment sessions per week.

6. The method of claim 5 wherein the low energy shockwave treatment protocol is configured according the number of active treatment sessions or the number of applied low energy shockwaves so as to cause an increased expression of Focal Adhesion Kinase (FAK) in and around said treatment area; and wherein said increased expression of FAK is proportional to the selected number of the active treatment sessions or the number of applied low energy shockwaves.

7. The method of claim 6 wherein the number of low energy shockwaves delivered in each session is gradually decreasing.

* * * * *